(12) United States Patent
Roby

(10) Patent No.: US 7,129,300 B2
(45) Date of Patent: Oct. 31, 2006

(54) BIOABSORBABLE ADHESIVE COMPOUNDS AND COMPOSITIONS

(75) Inventor: Mark S. Roby, Killingworth, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 397 days.

(21) Appl. No.: 10/176,280

(22) Filed: Jun. 19, 2002

(65) Prior Publication Data

US 2003/0032734 A1 Feb. 13, 2003

(51) Int. Cl.
*C08G 18/32* (2006.01)
*C08G 18/34* (2006.01)
*C08G 65/26* (2006.01)

(52) U.S. Cl. ...................... 525/408; 528/407
(58) Field of Classification Search ............ 525/408, 525/409; 528/84, 85
See application file for complete search history.

(56) References Cited

U.S. PATENT DOCUMENTS

| | | | |
|---|---|---|---|
| 3,879,493 A | 4/1975 | Mudde | |
| 3,903,232 A * | 9/1975 | Wood et al. | 264/157 |
| 3,975,350 A | 8/1976 | Hudgin et al. | 424/78 |
| 4,132,839 A * | 1/1979 | Marans et al. | 521/159 |
| 4,740,534 A * | 4/1988 | Matsuda et al. | 523/111 |
| 4,806,614 A | 2/1989 | Matsuda et al. | 528/59 |
| 4,994,542 A * | 2/1991 | Matsuda et al. | 528/70 |
| 5,065,752 A * | 11/1991 | Sessions et al. | 602/46 |
| 5,173,301 A * | 12/1992 | Itoh et al. | 424/448 |
| 5,204,110 A | 4/1993 | Cartmell et al. | 424/443 |
| 5,389,718 A | 2/1995 | Potter et al. | 524/591 |
| 5,457,141 A | 10/1995 | Matsuda | 523/111 |
| 5,578,662 A * | 11/1996 | Bennett et al. | 524/54 |
| 5,791,352 A | 8/1998 | Reich et al. | 128/898 |
| 5,948,427 A * | 9/1999 | Yamamoto et al. | 424/426 |
| 6,217,894 B1 | 4/2001 | Sawhney et al. | 424/426 |
| 6,290,729 B1 | 9/2001 | Sleplan et al. | 623/23.72 |
| 6,352,710 B1 | 3/2002 | Sawhney et al. | 424/426 |

* cited by examiner

Primary Examiner—Robert Sellers

(57) ABSTRACT

Bioabsorbable compounds which include a polyalkylene oxide backbone with two or more isocyanate substituents are useful as one component adhesives. Absorbable compositions useful as a two component adhesive contain a) a polyethylene oxide having two or more amine substituents with b) a bioabsorbable diisocyanate compound, or alternatively contain a) a polyethylene oxide having two or more isocyanate substituents with b) a bioabsorbable diamine compound, or, alternatively contain a) a bioabsorbable diisocyanate compound and b) a bioabsorbable diamine compound.

16 Claims, No Drawings

BIOABSORBABLE ADHESIVE COMPOUNDS AND COMPOSITIONS

BACKGROUND

1. Technical Field

This disclosure relates to bioabsorbable compounds and compositions useful as surgical adhesives and sealants.

2. Description of the Related Art

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that, in order for surgical adhesives to be accepted by surgeons, they must possess a number of properties. First, they must exhibit high initial tack and an ability to bond rapidly to living tissue. Secondly, the strength of the bond should be sufficiently high to cause tissue failure before bond failure. Thirdly, the adhesive should form a bridge, preferably a permeable flexible bridge. Fourthly, the adhesive bridge and/or its metabolic products should not cause local histotoxic or carcinogenic effects.

A number of adhesive systems such as alkyl cyanoacrylates, polyacrylates, maleic anhydride/methyl vinyl ethers, epoxy systems, polyvinyl alcohols, formaldehyde and gluteraldehyde resins and isocyanates have been investigated as possible surgical adhesives. None has gained acceptance because each fails to meet one or more of the criteria noted above. The principal criticism of these systems has been the potential toxicity problems they pose.

It would be desirable to provide novel metabolically-acceptable isocyanate-based adhesives and in particular metabolically-acceptable surgical adhesives. It would also be desirable to provide metabolically-acceptable surgical adhesives which are biodegradable. It would also be desirable to provide a method for closing wounds in living tissue by use of novel, metabolically-acceptable surgical adhesives which are low in toxicity as a consequence of their physical properties.

SUMMARY

A bioabsorbable compound is provided herein which includes a polyalkylene oxide backbone with two or more isocyanate substituents and which is useful as a one component adhesive. In particularly useful embodiments, the polyalkylene backbone has a branched or multi-arm structure. For example, in one embodiment the compound corresponds to the following formula (I):

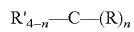  (I)

wherein the R' groups can be the same or different at each occurrence and are each individually chosen from the group consisting of —H and $C_1$ to $C_8$ alkylene-groups and the R groups can be the same or different at each occurrence and are each individually chosen from the group consisting of polyalkylene oxide groups and polyalkylene oxide groups substituted with at least one isocyanate group having formula (II) set forth below, with the proviso that at least two of the R groups are polyalkylene oxide groups substituted with at least one isocyanate group, and n is a number of from 2 to 4.

The group of formula (II) is an isocyanate group having the following structure:

  (II)

wherein A is a bioabsorbable group and is preferably derived from any monomer known to form a bioabsorbable polymer and n is from 1 to about 20. Suitable monomers from which the bioabsorbable group can be derived include glycolic acid, glycolide, lactic acid, lactide, 1,4-dioxane-2-one, 1,3-dioxane-2-one, ε-caprolactone and the like.

In another embodiment wherein the polyalkylene backbone has a branched or multi-arm structure, the compound corresponds to the following formula (III):

  (III)

wherein R is the same or different at each occurrence and are each individually chosen from the group consisting of —H, $C_1$ to $C_8$ alkylene groups, polyalkylene oxide groups and polyalkylene oxide groups substituted with at least one isocyanate group having formula (II) set forth above, with the proviso that at least two of the R groups are polyalkylene oxide groups substituted with at least one isocyanate group, and n is 2 to 6.

In another embodiment an absorbable composition useful as a two component adhesive is provided by combining a) a polyethylene oxide having two or more amine substituents with b) a bioabsorbable diisocyanate compound. The polyethylene oxide having two or more amine substituents includes a polyalkylene oxide backbone that is preferably branched or multi-armed. The bioabsorbable diisocyanate compound can be of the same structure as described above with respect to the one component adhesive embodiments, or an oligomeric bioabsorbable diisocyanate compound of the following formula (IV):

  (IV)

wherein A is as defined above, and p is 1 to 20 and q is 1 to 10.

In yet another embodiment an absorbable composition useful as a two component adhesive is provided by combining a) a polyethylene oxide having two or more isocyanate substituents with b) a bioabsorbable diamine compound. The polyethylene oxide having two or more isocyanate substituents includes a polyalkylene oxide backbone that is preferably branched or multi-armed. The bioabsorbable diamine compound can be of the same structure as described above with respect to the previous two component adhesive embodiment, or an oligomeric bioabsorbable diamine compound of the following formula (X):

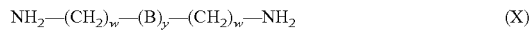  (X)

wherein B is a bioabsorbable group and w is 2 to 6 and y is 1 to 20. Bioabsorbable groups (B) include, for example, groups derived from any monomer known to form a bioabsorbable polymer (including but not limited to glycolic acid, glycolide, lactic acid, lactide, 1,4-dioxane-2-one, 1,3-dioxane-2-one, ε-caprolactone and the like) or groups derived from a diacid which will provide an absorbable linkage (including but not limited to succinic acid, adipic acid, malonic acid, glutaric acid, sebacic acid, diglycolic acid and the like).

The bioabsorbable compounds and compositions described herein are useful as surgical adhesives and/or sealants for joining portions of body tissue together or for joining surgically implantable devices to body tissue.

DETAILED DESCRIPTION OF PREFERRED EMBODIMENT(S)

The bioabsorbable compounds described herein are useful as surgical adhesives and sealants and include a polyalkylene oxide backbone substituted with one or more isocyanate groups. The polyalkylene oxide backbone can be derived from any $C_2$–$C_6$ alkylene oxide and can be homopolymeric or copolymeric. Thus, for example, the polyalkylene oxide backbone can be derived from ethylene oxide and be a polyethylene oxide (PEO) backbone. As another example, the polyalkylene oxide backbone can be derived from propylene oxide and be a polypropylene oxide (PPO) backbone. As yet another example, a combination of ethylene oxide and propylene oxide can be used to form a random or block copolymer as the backbone. The molecular weight of the polyalkylene oxide backbone should be chosen to provide desired physical characteristics to the final compound. Preferred backbones have molecular weights in the range of 500 to 20,000, preferably 1000 to 10,000, most preferably 2000 to 3500.

In particularly useful embodiments, the polyalkylene oxide backbone has a branched or multi-arm structure. For example, the polyalkylene oxide backbone can be the result of polymerizing alkylene oxide monomer in the presence of a multi-functional (e.g., polyhydric) initiator. Reaction conditions for producing branched or multi-arm polyalkylene oxide backbones are known to those skilled in the art.

In one embodiment the bioabsorbable compound corresponds to following formula (I):

wherein the R' groups can be the same or different at each occurrence and are each individually chosen from the group consisting of —H and $C_1$ to $C_8$ alkylene groups and the R groups can be the same or different at each occurrence and are each individually chosen from the group consisting of polyalkylene oxide groups and polyalkylene oxide groups substituted with at least one isocyanate group having formula (II) set forth below, with the proviso that at least two of the R groups are polyalkylene oxide groups substituted with at least one isocyanate group, and n is a number of from 2 to 4.

The group of formula (II) is an isocyanate group having the following structure:

-[A]$_n$-NCO    (II)

wherein A is a bioabsorbable group and is preferably derived from any monomer known to form a bioabsorbable polymer and n is from 1 to about 20. Suitable monomers from which the bioabsorbable group can be derived include glycolic acid, glycolide, lactic acid, lactide, 1,4-dioxane-2-one, 1,3-dioxane-2-one, ε-caprolactone and the like.

In another embodiment, the compound corresponds to the following formula (III):

wherein the R groups are the same or different at each occurrence and are each individually chosen from the group consisting of —H, $C_1$ to $C_8$ alkylene groups, polyalkylene oxide groups and polyalkylene oxide groups substituted with at least one isocyanate group having formula (II) set forth above, with the proviso that at least two of the R groups are polyalkylene oxide groups substituted with at least one isocyanate group, and n is 2 to 6.

While the isocyanate substituents are shown in formula (I) and formula (III) as being terminally located on the polyalkylene oxide arms, it should be understood that substitution of the isocyanate groups at one or more location along the polyalkylene oxide arms is also contemplated. Likewise, although a single isocyanate group per polyalkylene oxide arm is shown, it is contemplated that more than one and up to ten or more isocyanate groups per polyalkylene oxide arm may be present.

The number of isocyanate groups present on the polyalkylene oxide backbone is selected to provide desired physical characteristics to the compound upon exposure to moisture. A greater degree of substitution will provide greater cross-linking which will provide a material that exhibits less swelling and less compliance. A lower degree of substitution will yield a less cross-linked material having greater compliance.

The present compounds can be prepared by reacting a polyalkylene oxide backbone having two or more hydroxyl groups with a molar excess of diacid to provide a polyalkylene diacid. This will add the bioabsorbable group to the polyalkylene oxide backbone and provide free acid groups. Suitable diacids which will provide an absorbable linkage will be apparent to those skilled in the art and include succinic acid, adipic acid, malonic acid, glutaric acid, sebacic acid, diglycolic acid and the like. While the exact reaction conditions will depend upon the specific starting components, generally speaking the polyalkylene oxide backbone and the diacid are reacted at temperatures in the range of 25° C. to 150° C., for a period of time from 30 minutes to 24 hours at atmospheric pressure in the presence of a transesterification catalyst such as, for example stannous octoate, stannous chloride, diethyl zinc or zirconium acetylacetonate.

Once a diacid is formed, conversion thereof to an isocyanate can be accomplished by techniques within the purview of those skilled in the art. For example, the free acid groups can be reacted with thionyl chloride to produce the corresponding acyl chloride followed by reaction with sodium azide to provide isocyanate groups. This conversion is conducted utilizing a suitable solvent such as, for example, THF, chloroform or benzene.

Upon crosslinking, the present bioabsorbable compounds can be used as single component adhesives or sealants. Cross-linking is normally performed by exposing the compound to water in the presence of a catalyst, such as tertiary amine catalyst.

While not wishing to be bound by any theory, it is believed that the water reacts with the isocyanate groups of the present decarboxylates to the corresponding amine and carbon dioxide. The amine reacts with additional isocyanate to form polyurea which foams due to the simultaneous evolution of carbon dioxide thereby forming a porous, polymeric bridge.

The exact reaction conditions for achieving cross-linking will vary depending on a number of factors such as the particular bioabsorbable compound employed, the degree of isocyanate substitution, the specific isocyanate present on the polyalkylene backbone and the desired degree of cross-linking. Normally, the cross-linking reaction is conducted at temperatures ranging from 20° C. to about 40° C. for thirty seconds to about one hour or more. The amount of water employed will normally range from about 0.05 moles to 1 moles per mole of bioabsorbable compound. While water is a preferred reactant to effect cross-linking it should be understood that other compounds could also be employed either together with or instead of water. Such compounds include diethylene glycol, polyethylene glycol and diamines, such as, for example, diethylamino propanediol. Suitable catalysts for use in the cross-linking reaction include 1,4 diazobicyclo [2.2.2] octane, triethylamine, and diethylaminoethanol.

The amount of catalyst employed can range from about 0.005 grams to about 5.0 grams per kilogram of compound being cross-linked.

When the bioabsorbable compound is intended for implantation it is possible to effectuate cross-linking in situ using the water naturally present in a mammalian body or with added water. However, to more precisely control the conditions and extent of cross-linking, it may be advantageous to partially cross-link the compound prior to its use as an implant.

The bioabsorbable compounds described herein can also be cross-linked by the application of heat alone, or by exposure to diamine vapor. These cross-linking techniques are particularly useful when the compounds are to be used as a coating, rather than as an adhesive or sealant.

In another embodiment a composition useful as a tissue adhesive or sealant includes a polyalkylene oxide having one or more amine substituents combined with a bioabsorbable isocyanate compound.

The amine-substituted polyalkylene oxide can be derived from any $C_2$–$C_6$ alkylene oxide and can be homopolymeric or copolymeric. Thus, for example, the amine-substituted polyalkylene oxide can be derived from ethylene oxide and be an amine-substituted polyethylene oxide (PEO). As another example, the polyalkylene oxide can be derived from propylene oxide and be an amine-substituted polypropylene oxide (PPO). As yet another example, a combination of ethylene oxide and propylene oxide can be used to form a random or block copolymer as the amine-substituted polyalkylene oxide. The molecular weight of the amine-substituted polyalkylene oxide should be chosen to provide desired physical characteristics to the final composition. The molecular weight of the polyalkylene oxide backbone should be chosen to provide desired physical characteristics to the final compound. Preferred backbones have molecular weights in the range of 500 to 20,000, preferably 1000 to 10,000, most preferably 2000 to 3500.

In particularly useful embodiments, the polyalkylene oxide backbone has a branched or multi-arm structure. For example, the polyalkylene oxide backbone can be the result of polymerizing alkylene oxide monomer in the presence of a multi-functional (e.g., polyhydric) initiator. Reaction conditions for producing branched or multi-arm polyalkylene oxide backbones are known to those skilled in the art.

In one embodiment the amine-substituted polyalkylene oxide compound corresponds to following formula (IV):

$$R'_{4-n}\text{—C—}(R)_n \tag{IV}$$

wherein the R' groups can be the same or different at each occurrence and are each individually chosen from the group consisting of —H and $C_1$ to $C_8$ alkylene groups and the R groups can be the same or different at each occurrence and are each individually chosen from the group consisting of polyalkylene oxide groups and polyalkylene oxide groups substituted with at least one amine group, with the proviso that at least two of the R groups are polyalkylene oxide groups substituted with at least one amine group, and n is a number of from 2 to 4.

In another embodiment, the amine-substituted polyalkylene oxide compound corresponds to the following formula (V):

wherein the R groups are the same or different at each occurrence and are each individually chosen from the group consisting of —H, $C_1$ to $C_8$ alkylene groups, polyalkylene oxide groups and polyalkylene oxide groups substituted with at least one amine group, with the proviso that at least two of the R groups are polyalkylene oxide groups substituted with at least one amine group, and n is 2 to 6.

The amine groups in the compounds of formula (IV) and formula (V) can be terminally located on the polyalkylene oxide arms, or, alternatively, substitution of the amine groups at one or more location along the polyalkylene oxide arms. Likewise, although a single amine group per polyalkylene oxide arm is preferred, it is also contemplated that more than one and up to ten or more amine groups per polyalkylene oxide arm may be present.

The number of amine groups present on the polyalkylene oxide backbone is selected to provide desired physical characteristics to the compound upon exposure to moisture. A greater degree of substitution will provide greater cross-linking which will provide a material that exhibits less swelling and less compliance. A lower degree of substitution will yield a less cross-linked material having greater compliance.

The preparation of amine-substituted polyalkylene oxides is within the purview of those skilled in the art. In fact, suitable amine-substituted polyalkylene oxides are commercially available from Shearwater Polymers, Inc., Huntsville, Ala. Preferably, the amine-substituted polyalkylene oxide is a diamine.

The amine-substituted polyalkylene oxide is combined with a bioabsorbable isocyanate, preferably a bioabsorbable diisocyanate.

In one particularly useful embodiment, the bioabsorbable isocyanate that is combined with the amine-substituted polyalkylene oxide includes a polyalkylene oxide backbone substituted with one or more isocyanate groups. The polyalkylene oxide backbone can be derived from any $C_2$–$C_6$ alkylene oxide and can be homopolymeric or copolymeric. Thus, for example, the polyalkylene oxide backbone can be derived from ethylene oxide and be a polyethylene oxide (PEO) backbone. As another example, the polyalkylene oxide backbone can be derived from propylene oxide and be a polypropylene oxide (PPO) backbone. As yet another example, a combination of ethylene oxide and propylene oxide can be used to form a random or block copolymer as the backbone. The molecular weight of the polyalkylene oxide backbone should be chosen to provide desired physical characteristics to the final compound. Preferred backbones have molecular weights in the range of 500 to 20,000, preferably 1000 to 10,000, most preferably 2000 to 3500.

In particularly useful embodiments, the polyalkylene oxide backbone has a branched or multi-arm structure. For example, the polyalkylene oxide backbone can be the result of polymerizing alkylene oxide monomer in the presence of a multi-functional (e.g., polyhydric) initiator. Reaction conditions for producing branched or multi-arm polyalkylene oxide backbones are known to those skilled in the art.

In one embodiment the bioabsorbable isocyanate compound that is combined with the amine-substituted polyalkylene oxide compound corresponds to following formula (I):

$$R'_{4-n}\text{---}C\text{---}(R)_n \qquad (I)$$

wherein the R' groups can be the same or different at each occurrence and are each individually chosen from the group consisting of —H and $C_1$ to $C_8$ alkylene groups and the R groups can be the same or different at each occurrence and are each individually chosen from the group consisting of polyalkylene oxide groups and polyalkylene oxide groups substituted with at least one isocyanate group having formula (II) set forth below, with the proviso that at least two of the R groups are polyalkylene oxide groups substituted with at least one isocyanate group, and n is a number of from 2 to 4.

The group of formula (II) is an isocyanate group having the following structure:

$$\text{-}[A]_n\text{-NCO} \qquad (II)$$

wherein A is a bioabsorbable group and is preferably derived from any monomer known to form a bioabsorbable polymer and n is from 1 to about 20. Suitable monomers from which the bioabsorbable group can be derived include glycolic acid, glycolide, lactic acid, lactide, 1,4-dioxane-2-one, 1,3-dioxane-2-one, ε-caprolactone and the like.

In another embodiment, the absorbable isocyanate compound that is combined with the amine-substituted polyalkylene oxide compound corresponds to the following formula (III):

$$\begin{array}{c} R \\ | \\ H\text{---}(C)_n\text{---}H \\ | \\ H \end{array} \qquad (III)$$

wherein the R groups are the same or different at each occurrence and are each individually chosen from the group consisting of —H, $C_1$ to $C_8$ alkylene groups, polyalkylene oxide groups and polyalkylene oxide groups substituted with at least one isocyanate group having formula (II) set forth above, with the proviso that at least two of the R groups are polyalkylene oxide groups substituted with at least one isocyanate group, and n is 2 to 6.

While the isocyanate substituents are shown in formula (I) and formula (III) as being terminally located on the polyalkylene oxide arms, it should be understood that substitution of the isocyanate groups at one or more location along the polyalkylene oxide arms is also contemplated. Likewise, although a single isocyanate group per polyalkylene oxide arm is shown, it is contemplated that more than one and up to ten or more isocyanate groups per polyalkylene oxide arm may be present.

The number of isocyanate groups present on the polyalkylene oxide backbone is selected to provide desired physical characteristics to the compound upon exposure to moisture and/or to the multifunctional amine. A greater degree of substitution will provide greater cross-linking which will provide a material that exhibits less swelling and less compliance. A lower degree of substitution will yield a less cross-linked material having greater compliance.

In another embodiment, the bioabsorbable diisocyanate that is combined with the amine-substituted polyalkylene oxide compound has the following molecular structure:

$$\text{OCN-}(A)_p\text{-}(CH_2)_q\text{-}(A)_p\text{-NCO} \qquad (VI)$$

wherein A is a bioabsorbable group and is preferably derived from any monomer known to form a bioabsorbable polymer and p is from 1 to 20 and q is from 1 to 10. Preferably, the bioabsorbable group [A] is derived from a compound selected from the group consisting of glycolic acid, glycolide, lactic acid, lactide, ε-caprolactone, p-dioxanone, and trimethylene carbonate or substituted alkylene carbonates such as dimethyl trimethylene carbonate.

Those skilled in the art will readily envision reaction schemes for preparing useful bioabsorbable isocyanates. For example, bioabsorbable diisocyanates can be prepared by first preparing a bioabsorbable oligomer and then endcapping with isocyanate. Methods for the production of bioabsorbable oligomers and isocyanate endcapping are within the purview of those skilled in the art.

For example, the bioabsorbable oligomer can be prepared by drying purified monomer(s) used to form the bioabsorbable oligomer and then polymerizing at temperatures ranging from about 20° C. to about 220° C., preferably above 75° C., in the presence of an organometallic catalyst such as stannous octoate, stannous chloride, diethyl zinc or zirconium acetylacetonate. The polymerization time may range from 1 to 100 hours or longer depending on the other polymerization parameters but generally polymerization times of about 12 to about 48 hours are employed. In addition, an initiator such as, for example, diethylene glycol, is employed. Generally, the amount of initiator used will range from about 0.01 to about 30 percent by weight based on the weight of the monomer. Preferably, the initiator will be present in the reaction mixture in an amount from about 0.5 to about 20 weight percent based on the weight of the monomer.

Once the bioabsorbable oligomer is formed, isocyanate endcapping can be achieved by reacting the oligomer with a diisocyanate. Suitable diisocyanates include hexamethylene diisocyanate, diisocyanatolysine ethyl ester and butane diisocyanate. The conditions under which the oligomer is reacted with the diisocyanate may vary widely depending on the specific oligomer being endcapped, the specific diisocyanate being employed, and the desired degree of end capping to be achieved. Normally, the polymer is dissolved in a solvent and added dropwise to a solution of the diisocyanate at room temperature with stirring. The amount of diisocyanate employed can range from about 2 to about 8 moles of diisocyanate per mole of oligomer. Suitable reaction times and temperatures range from about 15 minutes to 72 hours or more at temperatures ranging from about 0° C. to 250° C.

As another example, bioabsorbable isocyanate compounds can be prepared by reacting a multifunctional (e.g., polyhydric) initiator with a molar excess of diacid to provide a diacid. This will add the bioabsorbable group to the initiator and provide free acid groups. Suitable diacids which will provide an absorbable linkage will be apparent to those skilled in the art and include succinic acid, adipic acid, malonic acid, glutaric acid, sebacic acid, diglycolic acid and the like. While the exact reaction conditions will depend upon the specific starting components, generally speaking the initiator and the diacid are reacted at temperatures in the range of 25° C. to 150° C., for a period of time from 30 minutes to 24 hours at atmospheric pressure in the presence of a transesterification catalyst such as, for example stannous octoate, stannous chloride, diethyl zinc or zirconium acetylacetonate.

Once a diacid is formed, conversion thereof to an isocyanate can be accomplished by techniques within the purview of those skilled in the art. For example, the free acid groups can be reacted with thionyl chloride to produce the corresponding acylchloride followed by reaction with sodium azide and heat to provide isocyanate groups.

Upon crosslinking, the present bioabsorbable compositions can be used as two component adhesives or sealants. Cross-linking is normally performed by combining the two components of the composition optionally in the presence of water and a catalyst, such as tertiary amine catalyst.

While not wishing to be bound by any theory, it is believed that the amine component of the composition reacts with the isocyanate component of the composition to form polyurea thereby forming a crosslinked polyalkylene oxide polymer.

The exact reaction conditions for achieving cross-linking will vary depending on a number of factors such as the particular components present in the bioabsorbable composition employed, the relative amounts of the components present in the bioabsorbable composition, the specific isocyanate present in the composition and the desired degree of cross-linking. Normally, the cross-linking reaction is conducted at temperatures ranging from 20° C. to about 40° C. for thirty seconds to about one hour or more. The amount of water employed will normally range from about 0 moles to 1 mole per mole of isocyanate compound in the composition. While water is a preferred reactant to effect cross-linking it should be understood that other compounds could also be employed either together with or instead of water. Such compounds include diethylene glycol, polyethylene glycol and diamines, such as, for example, diethylamino propanediol. Suitable catalysts for use in the cross-linking reaction include 1,4 diazobicyclo [2.2.2]octane, triethylamine, and diethylaminoethanol.

The amount of catalyst employed can range from about 0.005 grams to about 5.0 grams per kilogram of the composition being cross-linked.

When the bioabsorbable composition is intended for implantation cross-linking may optionally be effectuated in situ using the water naturally present in a mammalian body or with added water. However, to more precisely control the conditions and extent of cross-linking, it may be advantageous to partially cross-link the composition prior to its use as an implant.

The bioabsorbable compositions described herein can also be cross-linked by the application of heat alone, or by exposure to diamine vapor. These cross-linking techniques are particularly useful when the compositions are to be used as a coating, rather than as an adhesive or sealant.

In yet another embodiment a composition useful as a tissue adhesive or sealant includes a polyalkylenelene oxide having one or more isocyanate substituents combined with a bioabsorbable diamine compound.

The isocyanate-substituted polyalkylene oxide can be derived from any $C_2$–$C_6$ alkylene oxide and can be homopolymeric or copolymeric. Thus, for example, the isocyanate-substituted polyalkylene oxide can be derived from ethylene oxide and be an isocyanate-substituted polyethylene oxide (PEO). As another example, the polyalkylene oxide can be derived from propylene oxide and be an isocyanate-substituted polypropylene oxide (PPO). As yet another example, a combination of ethylene oxide and propylene oxide can be used to form a random or block copolymer as the isocyanate-substituted polyalkylene oxide. The molecular weight of the isocyanate-substituted polyalkylene oxide should be chosen to provide desired physical characteristics to the final composition. The molecular weight of the polyalkylene oxide backbone should be chosen to provide desired physical characteristics to the final compound. Preferred backbones have molecular weights in the range of 500 to 20,000, preferably 1000 to 10,000, most preferably 2000 to 3500.

In particularly useful embodiments, the polyalkylene oxide backbone has a branched or multi-arm structure. For example, the polyalkylene oxide backbone can be the result of polymerizing alkylene oxide monomer in the presence of a multi-functional (e.g., polyhydric) initiator. Reaction conditions for producing branched or multi-arm polyalkylene oxide backbones are known to those skilled in the art.

In one embodiment the isocyanate-substituted polyalkylene oxide compound corresponds to following formula (VIII):

(VIII)

wherein the R' groups can be the same or different at each occurrence and are each individually chosen from the group consisting of —H and $C_1$ to $C_8$ alkylene groups and the R groups can be the same or different at each occurrence and are each individually chosen from the group consisting of polyalkylene oxide groups and polyalkylene oxide groups substituted with at least one isocyanate group, with the proviso that at least two of the R groups are polyalkylene oxide groups substituted with at least one isocyanate group, and n is a number of from 2 to 4.

In another embodiment, the isocyanate-substituted polyalkylene oxide compound corresponds to the following formula (IX):

(IX)

wherein the R groups are the same or different at each occurrence and are each individually chosen from the group consisting of —H, $C_1$ to $C_8$ alkylene groups, polyalkylene oxide groups and polyalkylene oxide groups substituted with at least one isocyanate group, with the proviso that at least two of the R groups are polyalkylene oxide groups substituted with at least one isocyanate group, and n is 2 to 6.

The isocyanate groups in the compounds of formula (VIII) and formula (IX) can be terminally located on the polyalkylene oxide arms, or, alternatively, substitution of the isocyanate groups can be at one or more location along the polyalkylene oxide arms. Likewise, although a single isocyanate group per polyalkylene oxide arm is preferred, it is also contemplated that more than one and up to ten or more isocyanate groups per polyalkylene oxide arm may be present.

The number of isocyanate groups present on the polyalkylene oxide backbone is selected to provide desired physical characteristics to the compound upon exposure to moisture and/or to a diamine. A greater degree of substitution will provide greater cross-linking which will provide a material that exhibits less swelling and less compliance. A lower degree of substitution will yield a less cross-linked material having greater compliance.

The preparation of isocyanate-substituted polyalkylene oxides is within the purview of those skilled in the art. In fact, suitable isocyanate-substituted polyalkylene oxides are commercially available from Shearwater Polymers, Inc., Huntsville, Ala. Preferably, the isocyanate-substituted polyalkylene oxide is a diisocyanate.

The isocyanate-substituted polyalkylene oxide is combined with a bioabsorbable amine, preferably a bioabsorbable diamine.

In one particularly useful embodiment, the bioabsorbable amine that is combined with the isocyanate-substituted polyalkylene oxide is a compound of the following formula (X):

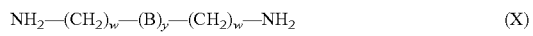

$$NH_2\text{—}(CH_2)_w\text{—}(B)_y\text{—}(CH_2)_w\text{—}NH_2 \qquad (X)$$

wherein B is a bioabsorbable group and w is 2 to 6 and y is 1 to 20. Bioabsorbable groups (B) include, for example, groups derived from any monomer known to form a bioabsorbable polymer (including but not limited to glycolic acid, glycolide, lactic acid, lactide, 1,4-dioxane-2-one, 1,3-dioxane-2-one, ε-caprolactone and the like) or groups derived from a diacid which will provide an absorbable linkage (including but not limited to succinic acid, adipic acid, malonic acid, glutaric acid, sebacic acid, diglycolic acid and the like).

Bioabsorbable amine compounds can be prepared by blocking the amine group on an alcohol amine and reacting the blocked alcohol amine with a diacid. This will add the bioabsorbable group to the alcohol amine and provide free amine groups.

Suitable diacids which will provide an absorbable linkage will be apparent to those skilled in the art and include succinic acid, adipic acid, malonic acid, glutaric acid, sebacic acid, diglycolic acid and the like. Suitable alcohol amines include, but are not limited to, $C_1$–$C_6$ alcohol amines such as, for example, ethanolamine and propanolamine.

Blocking of the amine group of the alcohol amine can be achieved using techniques well known to those skilled in the art. For example, the alcohol amine can be reacted with benzylchloroformate to block the amine group so that reaction takes place between the diacid and the hydroxyl group of the alcohol amine.

While the exact reaction conditions will depend upon the specific starting components, generally speaking the blocked alcohol amine and the diacid are reacted at temperatures in the range of 20° C. to 200° C., for a period of time from 30 minutes to 24 hours at atmospheric pressure in a suitable solvent such as, for example, THF. The resulting compound is reduced with hydrogen and a palladium catalyst which results in decarboxylation and provides a diamine.

Upon crosslinking, the present bioabsorbable compositions can be used as two component adhesives or sealants. Cross-linking is normally performed by combining the two components of the composition optionally in the presence of water and a catalyst, such as tertiary amine catalyst.

While not wishing to be bound by any theory, it is believed that the amine component of the composition reacts with the isocyanate component of the composition to form polyurea thereby forming a crosslinked polyalkylene oxide polymer.

The exact reaction conditions for achieving cross-linking will vary depending on a number of factors such as the particular components present in the bioabsorbable composition employed, the relative amounts of the components present in the bioabsorbable composition, the specific isocyanate present in the composition and the desired degree of cross-linking. Normally, the cross-linking reaction is conducted at temperatures ranging from 20° C. to about 40° C. for thirty seconds to about one hour or more. The amount of water employed will normally range from about 0 moles to 1 mole per mole of isocyanate compound in the composition. While water is a preferred reactant to effect cross-linking it should be understood that other compounds could also be employed either together with or instead of water. Such compounds include diethylene glycol, polyethylene glycol and diamines, such as, for example, diethylamino propanediol. Suitable catalysts for use in the cross-linking reaction include 1,4 diazobicyclo [2.2.2] octane, triethylamine, and diethylaminoethanol.

The amount of catalyst employed can range from about 0.005 grams to about 5.0 grams per kilogram of the composition being cross-linked.

When the bioabsorbable composition is intended for implantation cross-linking can optionally be effectuated in situ using the water naturally present in a mammalian body or with added water. However, to more precisely control the conditions and extent of cross-linking, it may be advantageous to partially cross-link the composition prior to its use as an implant.

The bioabsorbable compositions described herein can also be cross-linked by the application of heat alone, or by exposure to diamine vapor. These cross-linking techniques are particularly useful when the compositions are to be used as a coating, rather than as an adhesive or sealant.

In another embodiment, the isocyanate polymer composition can be chemically altered to provide a desired charge on the polymer. The presence of charged groups on the polymer can enhance wound healing in either hard or soft tissue. To impart a positive charge, a positive charge inducing reactant such as, for example, diethylethanolamine, can be introduced into the polymer. To impart a negative charge, the polymer may be reacted with a negative charge inducing reactant such as, for example, carboxymethanol.

The bioabsorbable compounds and compositions described herein are advantageously useful as a surgical adhesive or sealant, for example, for joining portions of body tissue together, or for adhering a surgical device such as a surgical mesh, fastener, implant, etc., to soft body tissue.

Upon contact with water, the bioabsorbable isocyanate polymer composition undergoes cross-linking and the isocyanate groups are converted to urea or urethane moieties, which promotes adhesion to hard and/or soft body tissue.

It will be understood that various modifications may be made to the embodiments disclosed herein. For example, the compositions in accordance with this disclosure can be

We claim:

1. A bioabsorbable compound of the formula:

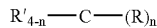

$$R'_{4-n}-C-(R)_n$$

wherein the R' groups can be the same or different at each occurrence and are each individually chosen from the group consisting of —H and $C_1$ to $C_8$ alkylene groups, n is a number of from 2 to 4, and the R groups can be the same or different at each occurrence and are each individually chosen from the group consisting of polyalkylene oxide groups and polyalkylene oxide groups substituted with at least one isocyanate group having the formula:

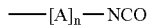

$$-[A]_n-NCO$$

wherein A is a bioabsorbable group and n is from 1 to about 20, with the proviso that at least two of the R groups are polyalkylene oxide groups substituted with at least one isocyanate group.

2. A bioabsorbable compound as in claim 1 wherein the isocyanate groups includes a bioabsorbable group derived from a monomer selected from the group consisting of glycolic acid, glycolide, lactic acid, lactide, 1,4-dioxane-2-one, 1,3-dioxane-2-one and ε-caprolactone.

3. A bioabsorbable compound as in claim 1 wherein the polyalkylene oxide groups substituted with at least one isocyanate group have a terminal isocyanate group.

4. A bioabsorbable compound as in claim 1 wherein the polyalkylene oxide groups are derived from one or more compounds selected from the group consisting of polyethylene oxide, polypropylene oxide and random or block copolymers of ethylene oxide and propylene oxide.

5. A bioabsorbable compound as in claim 4 wherein the molecular weight of the polyalkylene oxide groups is in the range of 500 to 20,000.

6. A bioabsorbable compound as in claim 4 wherein the molecular weight of the polyalkylene oxide groups is in the range of 1000 to 10,000.

7. A bioabsorbable compound as in claim 4 wherein the molecular weight of the polyalkylene oxide groups is in the range of 2000 to 3500.

8. A bioabsorbable compound as in claim 1 wherein the polyalkylene oxide group has a branched structure.

9. A bioabsorbable compound of the formula:

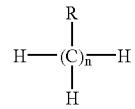

$$H-(C)_n-H \quad \text{(III)}$$

with R above and H below the central C.

wherein n is from 2 to 6 and the R groups are the same or different at each occurrence and are each individually selected from the group consisting of —H, $C_1$ to $C_8$ alkylene groups, polyalkylene oxide groups and polyalkylene oxide groups substituted with at least one isocyanate group having the formula:

$$-[A]_n\text{-NCO}$$

wherein A is a bioabsorbable group derived from a monomer selected from the group consisting of glycolic acid, glycolide, lactic acid, lactide, 1,4-dioxane-2-one, 1,3-dioxane-2-one and ε-caprolactone, and n is from 1 to about 20, with the proviso that at least two of the R groups are polyalkylene oxide groups substituted with at least one isocyanate group having the formula:

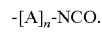

$$-[A]_n\text{-NCO}.$$

10. A bioabsorbable compound as in claim 9 wherein the polyalkylene oxide groups are derived from one or more compounds selected from the group consisting of polyethylene oxide, polypropylene oxide and random or block copolymers of ethylene oxide and propylene oxide.

11. A bioabsorbable compound as in claim 10 wherein the molecular weight of the polyalkylene oxide groups is in the range of 500 to 20,000.

12. A bioabsorbable compound as in claim 10 wherein the molecular weight of the polyalkylene oxide groups is in the range of 1000 to 10,000.

13. A bioabsorbable compound as in claim 10 wherein the molecular weight of the polyalkylene oxide groups is in the range of 2000 to 3500.

14. A bioabsorbable compound as in claim 9 wherein the polyalkylene oxide group has a branched structure.

15. A one component adhesive comprising a compound of claim 1.

16. A one component adhesive comprising a compound of claim 9.

* * * * *